Figure 1:
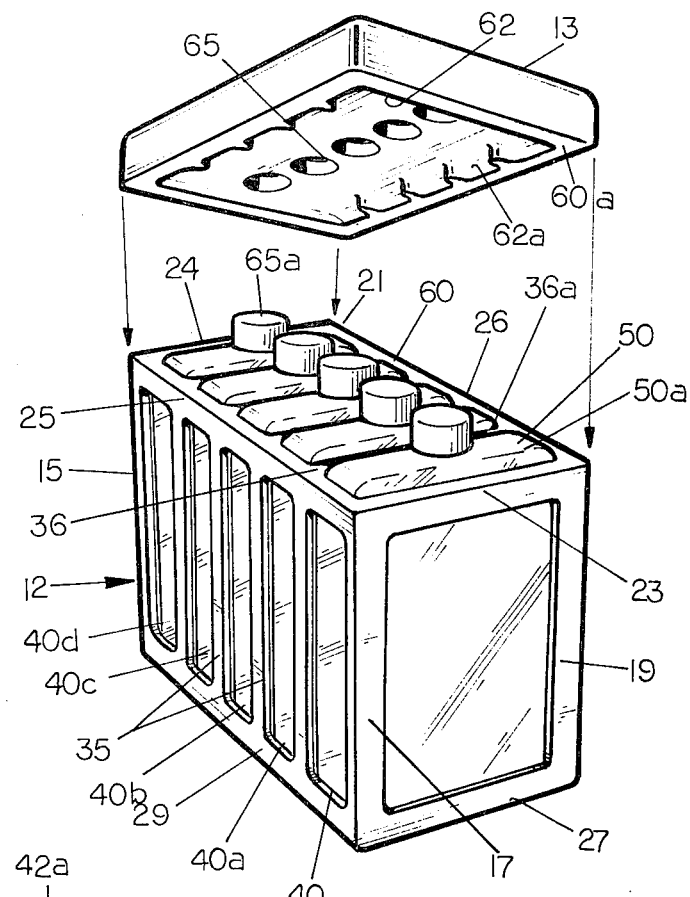

United States Patent [19]

Moss, III

[11] 4,143,764

[45] Mar. 13, 1979

[54] SHIPPER CONTAINER FOR FLASKS

[76] Inventor: L. Howard Moss, III, 5236 Vernadale St., Dayton, Ohio 45429

[21] Appl. No.: 724,997

[22] Filed: Sep. 20, 1976

[51] Int. Cl.² .......................................... B65D 25/04
[52] U.S. Cl. .................................. 206/429; 206/431; 206/45.31; 206/561; 220/23.83; 220/84; 220/85 H
[58] Field of Search .................... 220/23.83, 20, 20.5, 220/22, 21, 200, 85 H, 84, 9 F; 206/387, 526, 45.31, 45.34, 431, 429, 433, 561, 558

[56] References Cited

U.S. PATENT DOCUMENTS

| | | | |
|---|---|---|---|
| 1,995,310 | 3/1935 | Kruger | 220/21 |
| 2,695,723 | 11/1954 | Waterman | 220/84 |
| 2,963,193 | 12/1960 | Arthur | 220/21 |
| 3,009,564 | 11/1961 | Geloso | 220/22 |
| 3,358,825 | 12/1967 | Pullman | 206/438 |
| 3,365,260 | 1/1968 | Saxon | 206/526 |
| 3,401,535 | 9/1968 | Palmer | 220/9 F |
| 3,472,568 | 10/1969 | Southwick | 220/9 F |
| 3,710,900 | 1/1973 | Fink | 206/387 |
| 3,744,661 | 7/1973 | Fischer, Jr. | 220/21 |
| 3,907,116 | 9/1975 | Wolf et al. | 206/387 |

Primary Examiner—William Price
Assistant Examiner—Joseph Man-Fu Moy

[57] ABSTRACT

A shipping container and convenience rack for a plurality of culture flasks including an open-sided, generally cubic structure with internal slide-type separators defining singular compartments for a like plurality of flasks and featuring a lid having void recesses receptive of the closured mouths of the flasks to protect same and lend spatial stability in shipment.

8 Claims, 2 Drawing Figures

U.S. Patent      Mar. 13, 1979      4,143,764

SHIPPER CONTAINER FOR FLASKS

The present invention relates to a shipping receptacle for a plurality of culture flasks; the shipper container also serving as a convenience rack as used by the consumer. More particularly, the present invention relates to a shipping container adapted to receive and contain a plurality of 250 milliliter culture flasks in spaced protected relationship; the container desirably featuring a lid which augments the protective function for the individual tissue culture flasks.

Tissue culture flasks are usually formed of glass or a plastic such as methyl methacrylate, although any convenient material of construction can be employed. These flasks are used in the field of medicine, bacteriology, biology, chemistry and science generally for containing various tissue cultures for a period of time as to permit exposure of the tissue culture to any one of a variety of controlled environments; following which, comparative testing and analysis of the tissue culture can be performed. Of course, a variety of other uses are known to the art.

Flasks such as described are provided with closures and are presently marketed in large plastic bags formed of polyethylene which allow the containment of a large quantity of the flasks in random relationship within the bag for shipping from the manufacturer to the downstream marketing distribution entities such as jobber, distributor and, of course, ultimately the consumer, be it a hospital, industrial or academic laboratory, experimental station, biological research center or the like. As indicated, the flasks are then used for containment of any one of a variety of culture, cultures, culture mediums, etc., which are held for various periods of time and perhaps combined with other substances; following which, they are exposed to a variety of environments dictated by the particular experiment, purpose, etc. Since these are used for a scientific purpose, sterility is important and, as well, general absence of contamination. Furthermore, cleanliness, accuracy and responsible care in handling are factors which are desirably maintained at high levels to insure the reliability of the testing and observation involved in the particular experimentation, such as exposure to incubation conditions or the like. Lack of cleanliness and lack of sterility, on the other hand, adversely affects the culture or the culture medium and, in turn, adversely affects the reliability of the comparative testing, observations and results. These adverse and therefore undesirable conditions can be encountered during shipment and in later handling by the user. For example, the random loose packing of the culture flasks in polyethylene bags or shipment as described is quite unsatisfactory since the closures become loose due to physical contact and/or vibration, whereby the sterile conditions within are destroyed. This is not to mention the frequently encountered damage, breakage and simple lack of cleanliness. The handling of large numbers of individual culture flasks as necessary in the particular experimentation also gives rise to loss of sterility, contamination and lack of cleanliness, principally by reason of the mere numbers of flasks which must be individually transported hither and yon in makeshift fashion about the laboratory or the site of the particular experimentation involving the tissue culture flasks. In summation, it is observed that the shipping is a random packing arrangement, leading to adverse conditions, and the manual handling is random, leading to unreliable test results.

With the foregoing introduction, it may be stated that a principal object of the present invention is to provide a combined shipping package and convenience rack which significantly reduces the problems and difficulties encountered with random packing and random handling, either or both of which are unsatisfactory as described hereinabove.

It is yet another object of the present invention to provide a shipping package adapted and designed to safely contain, in isolated relationship, a plurality of sterile tissue culture flasks.

It is still another object of the present invention to provide such a shipping package which, following usefulness as a shipping package, is usable as a rack for transporting a plurality of appropriately sized tissue culture flasks about the laboratory or about the site in which the experimentation involving the tissue culture flasks is being performed and which can be used for transporting the plurality of flasks, either unfilled or filled, into and out of various incubators, gaseous tanks, ovens or the like to provide any variant exposure or environment as needed.

It is a significant object of the present invention to provide such a shipping package of multiple use or function which is of quite simple construction, is adapted therefore to be molded and accordingly is capable of production at low unit cost and therefore economically attractive to the ultimate consumer.

It is yet another object of the present invention to provide a shipping package which, in its ultimate usage as a multiple flask rack, is quite lightweight and accordingly very easily handled by personnel and at the same time is very utilitarian in the provision for separate compartments for the several flasks.

It is another object of the present invention to provide a structure of the type described which includes novel features of structure as promote and/or allow easy viewing of the flasks while fully within the rack in order to observe the contents, the color change or the condition of the culture without removing the flasks from the rack.

It is still another object of the present invention to provide such a package which includes a unique lid which features constructional contour and configuration as contactingly supports and positions the flasks in a manner which precludes shifting movement of the flasks or the closure as might lead to loss of the sterile condition within the closured flasks or breakage or damage.

The foregoing as well as other objects of the present invention will become apparent to those skilled in the art from the following detailed description taken in conjunction with the annexed sheet of drawings on which there is presented, for purpose of illustration only, one embodiment of the present invention.

IN THE DRAWINGS

Figure 2:
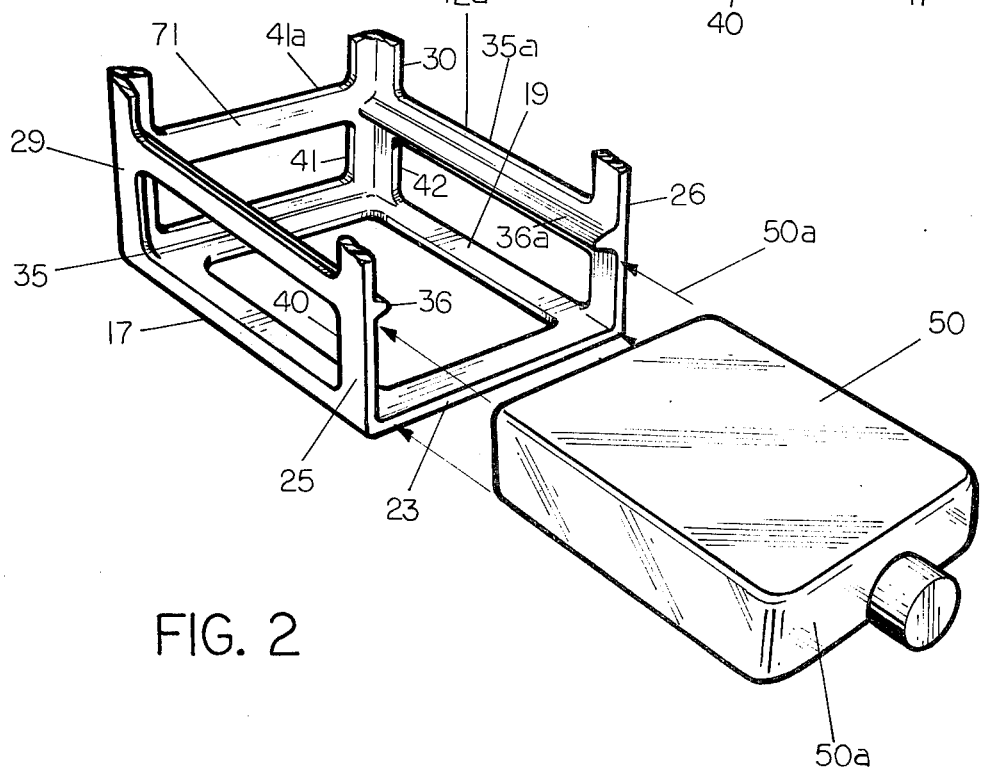

FIG. 1 is a three-quarter perspective view of the combination shipper package and rack of the present invention and with the lid portion shown suspended above the top of the package in order to show underside details of construction; and FIG. 2 is a three-quarter perspective view of the package turned 90° onto a side wall and with a major portion broken away in order to show interior details of structure and particularly showing a tissue culture flask in spaced lateral relationship, ready for insertion into the rack.

In its simplest embodiment, the present invention envisions a generally cubic, open-sided structure of relatively lightweight plastic which contains internally disposed guideways which, in concert with each other and other structural members, define a plurality of side-by-side cells or compartments for a like plurality of tissue culture flasks.

Reference may now be had to FIG. 1 wherein the shipper container identified by the reference numeral 11 is seen in upright position and composed of a generally box-like or cubic structure 12 and a lid 13. The box-like structure 12 is composed of four vertical corner members 15, 17, 19 and 21; the latter member 21 being to the rear in this view and therefore not seen. Integral with the spaced corner members are top edge members 23 and 24 in opposed relationship and 25 and 26 in opposed relationship; the four top edge members connecting with the upper extremities of the corner members. Reference numeral 27 identifies one lower or bottom edge member connecting corner members 17 and 19 situated in spaced parallel relationship with upper edge member 23. Reference numeral 29 identifies a lower edge member connecting corner members 15 and 17 in spaced parallel relationship with upper edge member 25. The other lower edge members which connect corner members 15 and 21 and corner members 21 and 19, respectively, and situated beneath upper edge members 24 and 26, respectively, cannot be seen.

Extending integrally between upper and lower edge pairs 25-29 are a plurality of spaced parallel strut members 35 which leave spaces or windows 40 between them and the adjoining corner members. Similarly, strut members 35a (FIG. 2) parallel to corner 19 extend between edge 26 and edge 30. For each strut 35, there is a corresponding strut 35a in opposed relationship. Each of the strut members 35 and 35a have integrally formed on their inner surface inwardly projecting linear projections 36 and 36a, respectively, which are, in effect, like drawer slides and serve to define closely spaced, isolated compartments for the plurality of culture flasks 50, as shown in FIG. 1.

Referring to FIG. 2, reference numeral 30 identifies a bottom edge former in spaced parallel relationship with the bottom edge former 29. As indicated, in FIG. 2, the structure 12 has been rotated 90° so that the corner members 17 and 19 are lying horizontal and the bottom edge 29 and, of course, its counterpart 30 are projecting normally upwardly. The major portion of the structure has also been broken away in order to show the interior rails 36 and 36a projecting inwardly to define separators between the lower compartment into which the culture flasks 50 fit if moved telescopically therewithin on the projection lines 50a. The rails 36 and 36a form opposed support edges for the second culture flask and separate it from the first flask in the lower compartment. A plurality of separate compartments are thus provided by similar projections 36 and 36a; certain of which can be seen in FIG. 1. FIG. 2 also illustrates clearly that the structure as defined provides three cutout regions or windows 40, 41 and 42 viewing the culture flasks and, more importantly, the interior thereof. Similarly, the structure includes a second set of windows 40a, 41a and 42a. Other identical window sets such as 40b and 40c allow full viewing of the flasks.

The bottom edge formers 29 and 30 in spaced relationship are joined by spaced linear frames 71 which are integral with the bottom edge formers. As referred to earlier, in FIG. 2, the bottom edge formers 29 and 30 are shown vertically at the rear, with the one linear frame member 71 connecting them. The other linear frame members 71 are not seen because of the cutting away of the remainder of the structure in this view. They can neither be seen in FIG. 1 because they are behind and at the bottom of the structure in the view as shown. There is a linear frame member 71 for each of the side rails 35 or 35a and they lie in general alignment with these members 35 and 35a and, from the drawings and the foregoing, it will be appreciated that the latter cooperate to define a plurality of cutout or window sets as previously described and identifield by the reference numerals 41, 41a, etc.

Referring again now to FIG. 1, the structure is shown in position for inserting flasks which are shown with the flask shoulders and closures in the upwardly facing position. The top edge members 23, 24, 25 and 26 cooperate to form an upwardly facing closed rectangular flat or "land" surface 60. Similarly, lid 13 contains a peripheral flat or "land" surface 60a facing downwardly, which is congruent to the upwardly facing "land" surface 60, and accordingly allows flush abutment of the surfaces 60 and 60a. The lid or closure 13 also has an under surface which is recessed, as at 62, to define a generally rectangular region accommodating the shoulder regions 50a of the culture flasks 50 which projects slightly above the horizontal plane defined by the "land" surface closure area 60. Additionally, the closures contain a row of circular cavities 65 which are in such spaced relationship as to receive the closured necks 65a of the tissue culture flasks 50 in loosely snug relationship. Spaced lateral edges 62a of the recess 62 are notched, as shown, to accommodate the shoulders 50a of the tissue culture flasks.

For shipping purposes, the closured flasks with sterile conditions within are located in the receptacle 12 in the manner shown in FIG. 1, whereupon the lid 13 is lowered downwardly in a manner to embrace the closured necks and with the surface 60a flush on the surface 60 of the receptacle 12. Any convenient securement can be employed to fasten the lid onto the receptacle; for example, tape or adhesive or such other securement as would be appropriate. While the package of culture flasks as shown includes 5 compartments for 5 tissue culture flasks, the structure may be designed and molded to contain 6 or even 12 tissue culture flasks. With the structure as described, a plurality of such packages of tissue culture flasks may be further boxed, 6, 12 or a larger number, into a larger box and shipped to the customer. The packages can be removed and stored on storage shelves for access and use as needed. The lids can then be easily removed, providing access to the individual tissue culture flasks.

In use, the receptacle 12 may be turned 90° to the position shown in FIG. 2, allowing the structure to assume the function of a rack of vertically stacked tissue culture flasks which may be withdrawn from the structure as needed or desired. Of course, the receptacle may be left as in its position shown in FIG. 1, with the tissue culture flasks still easily removable without contact with the adjoining flasks. The flasks can be opened by removing the closure, providing access to the maintained sterile conditions within. The desired culture medium can then be inserted into one or more of the flasks which can be reclosured if desired and reinserted into the rack and transported from place to place within the laboratory or wherever being used.

In accordance with one embodiment of the present invention, the box-like structure 12 is formed of an extremely lightweight foam-like material, providing structural rigidity but at the same time vibration-insulation properties. One such material is a generally white foam-like material formed from polystyrene beads which are heat-activatable within a mold of the desired configuration wherein the beads melt, expand and unify into the structure defined by the void of the mold cavity.

The structure is of relatively simple design and an appropriate mold is readily made in a manner well known in the art to provide a single or multiple cavity mold defining the structure 12. Where more permanence, resistance to heat and even to physical impact is desired, the box-like structure may be formed of stronger plastics, such as the amine-aldehyde condensation products, and where extreme impact resistance is desired, the so-called "ABS" polymers formed of acrylonitrile, butadiene and styrene may be desirable. Polymers of this type would be desirable not only from the standpoint of their inherent strength but also the deep draw capabilities in terms of the molding of the structure. The foam structure referred to hereinabove by its nature is opaque but the configuration and structure as defined, particularly featuring the corner and edge members, leave considerable voids, serving as windows and thus allowing observation of the culture flasks and, more importantly, the interior. In certain applications, the box-like structure is desirably molded of a plastic, such as methyl methacrylate or polyvinyl chloride or the like, which are inherently transparent and accordingly would impart to the ultimate structure an even greater visibility quotient or index as might be necessary or desirable for particular applications; that is, for particular research and/or comparative testing.

The rack-like support structure feature of the combination package of the present invention provides extreme utility in the use of the tissue culture flasks about the laboratory or other situs of use. The lid can be removed, with the package providing the user with the assurance that the flasks are in sterile condition by reason of the careful packaging in contrast to the loose random packing normally used as described earlier herein. Furthermore, a closure may be removed and a particular culture medium poured into the flasks with reliability and security as it is held in its vertical upright position by the structure itself. The closure can be reapplied and succeeding flasks can be filled with the appropriately desired culture medium. Reliability is thus enhanced as compared to individual handling of the flasks for filling purposes. The drawer-like compartments also provide a convenient system of indexing as their particular series arrangement is fixed and cannot be confused as could occur in individual handling of 5 or 6 flasks with varying amounts of a culture medium or with varying amounts of a test specimen introduced with the culture medium. At the same time, the filling proceeds with much more sureness since the flasks are held relatively stable in the rack package, albeit a flask can be removed for closer inspection if desired. Once the flasks in the rack package have been filled, the closures can be reapplied as needed and the plurality of flasks carried as a singular unit or group in the package to wherever desired in the laboratory.

Albeit not shown, in a preferred embodiment of the present invention, the cutouts or windows 41 in the bottom of the package as shown in FIG. 1 are provided with slightly upstanding, surrounding minor walls or edges. These walls or edges, in cooperation with the bottom edge formers, confine a modest amount of spillage from running through the window or cutout to the table top or contaminating adjoining or lower sets of flask packages in a particular environmental enclosure, such as an incubator or the like. Ideally, all of the cutouts or windows would be provided with surrounding minor walls or edges normal to the plane of the cutout or window to confine spillage and therefore minimize contamination and enhance cleanliness.

In further use of the package, after filling, the lid may be reapplied and the upper surface used as a stable platform for vertical stacking of a variety of like packages where desired.

It is also a desirable feature of the present invention that all of the outer surfaces are planar and the package is of generally cubical configuration so that multiple closure packages are block-like and can be stacked reliably and surely on almost any surface for usage convenience in and around the laboratory, enabling thereby handling of multiple flasks in a convenient assembled array as opposed to manual handling of individual flasks.

While the invention has been described in connection with a tissue culture flask of a stated volume, it will be appreciated that the concepts and features of construction and utility as described herein can be expanded to a variety of other flasks and containers as desirably employed in large numbers in a variety of arts. Accordingly, all of the obvious modifications and adaptations for obvious uses and applications are intended to be fully covered unless such adaptations and variations would do violence to the language of the appended claims.

I claim:

1. A combination shipping package and convenience rack for a plurality of tissue culture flasks having top, bottom, end and side walls and a closured neck opening extending outwardly from said top wall, said combination comprising:
   an open, six-side, box-like structure defined by corner, top edge and bottom edge members in spaced relationship, said structure including a plurality of interior slide or rail segments in opposed relationship on either side of said structure serving as separators and defining, in aggregate with each other and adjoining corner members, a plurality of separate compartments receptive of a like plurality of tissue culture flasks, said edge members and rail segments being in mutually spaced relationship to define voids or windows exposing all bottom, end and side walls of said flasks excepting those side walls adjacent an adjoining flask, and
   a generally planar lid for said box-like structure, said lid fitting flushly onto the top edge members of said box-like structure and having an under surface containing a plurality of void recesses adapted to receive the closured necks extending from said top wall of said culture flasks located in said compartments and thereby enhance the spatial stability of said flasks in said compartments and the relative isolations to avoid accidental breakage.

2. The invention as claimed in claim 1, wherein said structure corner members are of a dimension such that a shoulder region of said flask extends slightly beyond the top edge members and said lid includes recesses adapted to receive said shoulders.

3. The invention as claimed in claim 1, wherein said box-like structure members are of unitary formation.

4. The invention as claimed in claim 3, wherein said structure is formed of a foam-like material of vibration-insulation properties.

5. The invention as claimed in claim 4, wherein said structure corner members are of a dimension such that a shoulder region of said flask extends slightly beyond the top edge members and said lid includes recesses adapted to receive said shoulders.

6. The invention as claimed in claim 3, wherein said box-like structure is formed of a transparent, moldable material.

7. The invention as claimed in claim 5, wherein all sides are essentially normal to any adjoining side.

8. The invention as claimed in claim 7, wherein said voids or windows include surrounding minor walls to confine spillage.

* * * * *